US008219982B2

(12) United States Patent
Harkanyi et al.

(10) Patent No.: US 8,219,982 B2
(45) Date of Patent: Jul. 10, 2012

(54) METHOD FOR ORGANIZING THE SOFTWARE OF A FLUID MANAGEMENT SYSTEM

(75) Inventors: Gabor Harkanyi, Budapest (HU); Tibor Osztodi, Budapest (HU); Gunter Niemetz, Melsungen (DE)

(73) Assignee: B. Braun Medizintechnologie GmbH, Melsungen (DE)

( * ) Notice: Subject to any disclaimer, the term of this patent is extended or adjusted under 35 U.S.C. 154(b) by 1584 days.

(21) Appl. No.: 11/651,192

(22) Filed: Jan. 9, 2007

(65) Prior Publication Data

US 2007/0173979 A1    Jul. 26, 2007

(30) Foreign Application Priority Data

Jan. 17, 2006  (EP) .................................... 06100419

(51) Int. Cl.
| | |
|---|---|
| *G06F 9/44* | (2006.01) |
| *A61M 37/00* | (2006.01) |
| *A61N 1/30* | (2006.01) |
| *A61K 9/22* | (2006.01) |
| *G05D 7/00* | (2006.01) |
| *G05D 11/00* | (2006.01) |

(52) U.S. Cl. ..................... 717/168; 717/173; 604/890.1; 604/19; 604/4.01; 700/282

(58) Field of Classification Search ........................ None
See application file for complete search history.

(56) References Cited

U.S. PATENT DOCUMENTS

| | | | | |
|---|---|---|---|---|
| 2004/0225252 | A1* | 11/2004 | Gillespie et al. | 604/19 |
| 2006/0090159 | A1* | 4/2006 | Kondo | 717/168 |
| 2006/0101461 | A1* | 5/2006 | Han | 717/174 |

FOREIGN PATENT DOCUMENTS

| | | |
|---|---|---|
| DE | 44 08 544 A1 | 9/1995 |
| EP | 0 457 940 A1 | 11/1991 |
| EP | 0 750 766 B1 | 1/1997 |
| EP | 1 227 854 B1 | 8/2002 |

* cited by examiner

*Primary Examiner* — Lewis A Bullock, Jr.
*Assistant Examiner* — Mark Gooray
(74) *Attorney, Agent, or Firm* — RatnerPrestia

(57) ABSTRACT

A method and device for organizing the software of a fluid management system is disclosed. The processor system of a machine for the treatment of a patient is provided with an interface for connection to an external data storage device. The software of the processor system is divided into a treatment software for controlling and monitoring the treatment of a patient and a tool software for controlling and monitoring the service and/or production activities. In the processor system, the treatment software being stored in the processor system as resident software and the tool software being stored in the processor system as non-resident software. Moreover, updates can be performed with the external data storage device.

16 Claims, 1 Drawing Sheet

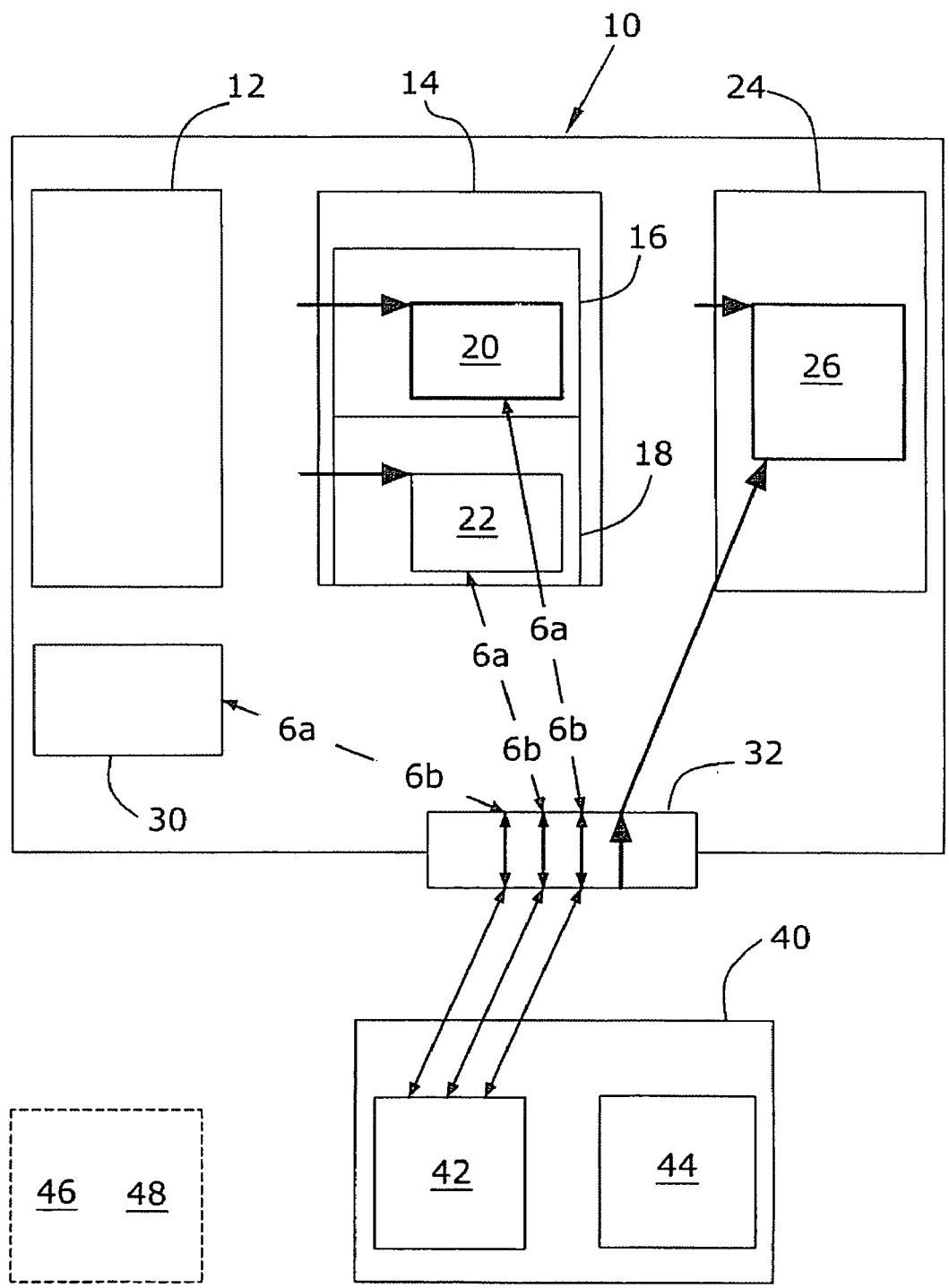

METHOD FOR ORGANIZING THE SOFTWARE OF A FLUID MANAGEMENT SYSTEM

FIELD OF THE INVENTION

The invention refers to a method for organizing the software of a fluid management system that includes at least a processor system with a CPU, a memory and software.

DESCRIPTION OF RELATED ART

A fluid management system should be conceived in particular as a medical treatment device for performing an extracorporeal blood treatment such as hemodialysis or hemofiltration. Here, a body fluid of the patient, e.g. blood, is subjected to an extracorporeal treatment, using a dialyzing liquid, for example. Such fluid management systems are subject to high standards regarding reliability and accuracy. Should these standards not be met, substantial risks to a patient can ensue. Therefore, the software that is loaded into the processor system is very complex. Roughly divided, it comprises treatment software and tool software. The treatment software includes the treatment programs the patient is subjected to, whereas the tool software comprises service and production programs. The treatment software has to be updated every once in a while, for which purpose a part or the entire treatment software is removed from the device and replaced with another treatment software.

EP 1 227 854 B1 describes a software update for a medical fluid management device, wherein, in a software updating mode, it is determined, with consideration to the existing versions of the software programs and/or the existing processor systems, which. software programs are to be loaded for which processor system via the data input device before initiating the loading of the software programs into the respective processor systems.

Further, DE 44 08 544 C2describes a method for installing software components on data processing means acting as target computers. Here, an auxiliary program, resident on the target computer or previously transmitted by a supply system, transmits an operating system prepared for the following steps to the target computer, where the auxiliary program is installed and started.

EP 0 457 940 A1describes the download of software into a medical monitor by means of an additional box.

A medical fluid management system requires a lot of memory capacity. A part of the memory capacity is used for treatment software that concerns a dialysis treatment, for example. The treatment not only has to be controlled and monitored, but is must also be documented in detail. Further, an authorization procedure is required sometimes, wherein a number of people have to enter their identification codes into the computer to be able to make certain treatment settings at the machine.

Another part of the device software may be referred to as tool software. This includes the service and production activities. The necessity for an update of the device software is mostly caused by the tool software. In contrast therewith, the treatment software is affected much less frequently.

SUMMARY OF THE INVENTION

One aspect of the present invention provides a method that facilitates the management and the updating of the software of a processor system.

According to the invention, the software is divided into a treatment software controlling and monitoring the treatment of a patient and a tool software controlling and monitoring the service and production activities, and that the processor system stores the treatment software as a resident software and the tool software as a non-resident software.

The invention is based on the idea that in a medical fluid management system about 20% of the memory capacity are needed for the treatment software, whereas about 80% are required for the tool software. The tool software requires updates much more frequently than the treatment software. Thus, the processor is loaded only with the treatment software as resident software, whereas the tool software is stored outside the processor system.

Resident software is software that is installed permanently, whereas non-resident software is deleted when the power supply or the device are turned off. During the treatment of a patient, the processor system includes only the treatment software. During the manufacture of the machine and during maintenance, however, the tool software is needed. When being manufactured, the machine is started up in steps during the so-called run-in-stress, when the pumps are tested in particular. For example, temperatures and pressures are also monitored in the process, and calibration data are obtained. The service activities include checking and maintaining the machine, malfunction diagnostics and the determination and extraction of trends. The maintenance technician installing the tool software has the external data storage device for transferring the tool software to the processor system. Thus, the processor system can do with a low capacity memory, because the tool software does not have to be stored permanently.

The invention allows for a detailed documentation of the treatment software for the patient treatment process, while the tool software is excepted from documentation. This amounts to an overall reduction of the documentation effort, and the authorization procedures that regard only the treatment software are reduced as well. The invention especially facilitates the updating of software. The software being divided into at least two components, i.e. treatment software and tool software, only the treatment software needs to be replaced with the update. It is even possible to perform an update of the tool software outside the processor system, for example, in the external data storage device or in a separate PC storing the tool software including the input and output file. During this update, the processor system of the machine is not blocked so that it can be used for patient treatment.

The resident software stored in the processor system can also be updated. This update is preferably performed with the external data storage device. To this end, the processor system is adapted to transfer information about its stored software and data to the external data storage device. The external data storage device may also be used to sample treatment information from the processor system. The input/output of the external data storage device is controlled either by a resident or a non-resident executable software of the processor system. Thus, the external data storage device does not necessarily require a processor of its own. Generally, a storage function will suffice. As an alternative, it is possible to provide the external data storage device with a processor of its own and to control the input/output by the own processor system.

In the processor system, the treatment software is stored and executed as resident software, whereas the tool software is loaded, stored and executed as non-resident software.

The tool software may be divided into functions, such as software update, service support, production support, so that the memory space in the processor system only has to be of the size of a partial function respectively used for the present operation. The invention further refers to a patient treatment machine with at least one processor system including a CPU, a memory and software stored therein. Such a patient treatment machine is defined by claim 11.

The dependent claims respectively refer to useful embodiments or developments of the subject matters of claims 1 and 11.

BRIEF DESCRIPTION OF THE DRAWINGS

The following is a detailed description of an embodiment of the invention with reference to the sole drawing.

FIG. 1 shows a block diagram of a processor system according to the present invention.

DETAILED DESCRIPTION OF A PREFERRED EMBODIMENT

The processor system 10 is a computer representing parts of the control and monitoring unit of a fluid treatment machine (not illustrated) for the extracorporeal blood treatment of a patient. The blood treatment machine is a dialysis machine or a machine for the treatment of blood plasma, for example.

The processor system 10 includes a microcontroller with a CPU 12 and a working memory. Further, the processor system includes a first memory 14 for resident programs and a second memory 24 for non-resident programs. The first memory 14 includes a first memory portion 16 and a second memory portion 18. The first memory portion 16 is a non-volatile memory for storing a firmly integrated BIOS software (Basic Input/Output System) 20.

The second memory portion 18 of the first memory 14 includes a resident executable program 22.

The second memory 24 is a RAM for storing non-resident programs and data. Among others, it includes the non-resident tool software 26 and data.

Further, the processor system 10 comprises peripheral devices 30, such as a hard disc, a keyboard, a monitor, a printer and the like.

The memories 14 and 24 as well as the peripheral devices each communicate bidirectionally with the CPU 12 and an interface 32. Through a plug system, an external data storage device 40 can be connected to the interface 32. This includes both input/output files 42 of the treatment software and of the tool software as well as execution code files for the treatment software and BIOS, and execution code files 44 for the tool software.

A memory, which is separately provided in the external data storage device 40, stores the tool software, i.e. a software 46 for the service activities and a software 48 for the production activities. Both software programs can be supplied to the processor system 10 from the external data storage device 40. The software program 20 for loading and starting the non-resident tool software 26 is a BIOS that is not deleted when the processor system is switched off. The program is executed under control of the CPU 12. The software program 22 for executing the resident treatment software is started by the BIOS 20 and is a software program executed under control of the CPU 12 and being preserved when the processor system is switched off.

The software programs regarding the service activities or the production activities belong to the non-resident software programs 26. These software programs are loaded and started by the BIOS 20. The software updating of the resident programs 20 and 22 also is part of the service programs.

Of the double arrows 6a and 6b, the direction 6b indicates the data transfer to the external data storage device 40 and the direction 6a indicates the loading of a software program and the data transfer from the external data memory device 40 to the respective internal memory.

The BIOS 20 forms the integrated software program part of the processor system from the manufacture on. An upgrade can be made thereto through the external data storage device 40. The BIOS software 20 is started by a signal generated by a hardware after the device has been turned on, and in turn loads and starts either the non-resident software 26 or the resident software 22. Via the interface 32, the resident software 22 and the non-resident software 26 may load data and programs into the memory 24 from the external data storage device or store data in the memory 40.

The update of the treatment software is effected in the following steps:

BIOS 20 loads a specific program for communication with the external data storage device 40 from the external data storage device 40 into the memory 24 and starts this program for the execution of the loading of the execution code file 44 from the external data storage device 40 and for storage into the non-resident memory 24 as an update program 26.

BIOS 20 starts the update program 26.

The update program 26 performs the replacement of the treatment software 22 by storing the file or the files from the memory for the input files 42 into the resident memory 18 for the treatment software 22.

The external data storage device 40 preferably is a memory stick or a flash drive adapted to be connected to the USB port of the processor system 10. Other possible external data storage devices 40 include floppy discs, CDs, DVDs, HDDs (hard disc drives) or external computers such as a laptop, for example. Moreover, the software programs 46 and 48 can be supplied to the external data storage device 40 or directly to the interface 32 via a data network, e.g. a LAN in the form of an Ethernet.

Although the invention has been described and illustrated with reference to specific illustrative embodiments thereof, it is not intended that the invention be limited to those illustrative embodiments. Those skilled in the art will recognize that variations and modifications can be made without departing from the true scope of the invention as defined by the claims that follow. It is therefore intended to include within the invention all such variations and modifications as fall within the scope of the appended claims and equivalents thereof.

What is claimed is:

1. A method for organizing the software of a fluid management system comprising at least one processor system with a CPU, a memory means and software stored therein, executing, by the fluid management system, a treatment software for controlling and monitoring fluid flow of the fluid management system during a treatment period of a patient, the treatment software being installed in a first memory device of the processor system as resident software which is maintained when a power supply of the fluid management system is turned off; and executing, by the fluid management system, tool software for testing an operation of the fluid management system during a testing period of the fluid management system and for updating the treatment software in the first memory device, the tool software being loaded from an external device and installed in a second memory device of the processor system as non-resident software which is not maintained when the power supply of the fluid management system is turned off;

wherein the tool software is loaded by system software of the fluid management system after the fluid management system is turned on.

2. The method of claim 1, wherein the non-resident software also includes a software for the execution of updates of the resident software.

3. The method of claim 1, wherein an external data storage device is provided that is adapted to be connected to the processor system and to load the non-resident software into the processor system.

4. The method of claim 2, wherein the processor system is adapted to transmit information about the software and data stored to the external data storage device.

5. The method of claim 3, wherein the resident software also includes a program loading a specific program for the connected external data storage device from the external data storage device, stores the same as a non-resident software and starts it.

6. The method of claim 3, wherein the external data storage device is used to store treatment information and/or service information from the processor system.

7. The method of claim 3, wherein the external data storage device is used for an update of the resident software.

8. The method of claim 3, wherein the input/output of the external data storage device is controlled by a resident executable software of the processor system.

9. The method of claim 3, wherein the input/output of the external data storage device is controlled by a non-resident executable software of the processor system.

10. The method of claim 3, wherein the input/output of the external data storage device is controlled by a processor of the external data storage device using an executable software stored in the external data storage device.

11. A machine for treating a patient comprising at least one processor system with a CPU, a memory means and software stored therein, wherein the software includes:

a treatment software for controlling and monitoring fluid flow of the fluid management system during treatment period of a patient, the treatment software being installed in a non-volatile memory device of the processor system, and a tool software for testing an operation of the fluid management system during a testing period of the fluid management system and for updating the treatment software in the non-volatile memory device, the tool software being loaded from an external device and installed in a volatile memory device of the processor system;

wherein the tool software is loaded by system software of the fluid management system after the fluid management system is turned on.

12. The machine of claim 11, wherein an external data storage device is provided that is adapted to be connected to the processor system and includes the treatment software and the tool software.

13. The machine of claim 12, wherein the external data storage device is an erasable memory, in particular a memory stick.

14. The machine of claim 12, wherein the external data storage device includes a processor.

15. The machine of claim 11, wherein the treatment period and the testing period are separate periods.

16. The method of claim 1, wherein the treatment period and the testing period are separate periods.

* * * * *